United States Patent [19]

Inoue et al.

[11] Patent Number: 4,920,134
[45] Date of Patent: Apr. 24, 1990

[54] 2-O-PYRIMIDINYL GLYCEROL DERIVATIVES

[75] Inventors: Keizo Inoue, Tokyo; Hiroaki Nomura; Eiko Imamiya, both of Osaka, all of Japan

[73] Assignee: Takeda Chemical Industries, Ltd., Osaka, Japan

[21] Appl. No.: 227,550

[22] Filed: Aug. 3, 1988

[30] Foreign Application Priority Data

Aug. 7, 1987 [JP] Japan ................................. 62-198455
Mar. 23, 1988 [JP] Japan ................................. 63-70338

[51] Int. Cl.$^5$ .......................................... C07D 239/34
[52] U.S. Cl. .................................. 544/316; 514/252; 514/269; 514/274; 544/120; 544/122; 544/123; 544/216; 544/238; 544/239; 544/240; 544/241; 544/295; 544/319; 544/357; 544/408
[58] Field of Search ................ 544/316, 319, 295, 123

[56] References Cited

U.S. PATENT DOCUMENTS

| | | | |
|---|---|---|---|
| 4,027,027 | 5/1977 | Jeggi | 544/316 |
| 4,294,966 | 10/1981 | Zergenyi | 544/316 |
| 4,438,128 | 3/1984 | Wiedemann | 544/295 |
| 4,460,588 | 7/1984 | Serban | 544/316 |
| 4,618,609 | 10/1986 | Acker | 544/316 |
| 4,731,373 | 3/1988 | Barner | 514/311 |

FOREIGN PATENT DOCUMENTS 0094586 11/1983 European Pat. Off. .
0109255 5/1984 European Pat. Off. .
0142333 5/1985 European Pat. Off. .
0238202 9/1987 European Pat. Off. .

OTHER PUBLICATIONS

Chem. Abstr., vol. 109, Entry 93527j, abstracting EP 254,540, pub. 27 Jan. 1988.

Primary Examiner—Donald G. Daus
Attorney, Agent, or Firm—Wegner & Bretschneider

[57] ABSTRACT

Novel compounds having the formula:

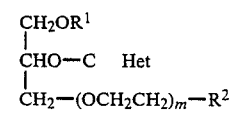

wherein

—C Het represents a nitrogen-containing aromatic 6-membered ring; $R^1$ represents a higher alkyl group which may be substituted; $R^2$ represents a tertiary amino group or a quaternary ammonium group; and m represents 2 or 3; and salts thereof have superior antitumor activities including differentiation-inducing activity, and are useful as antitumor agents.

12 Claims, No Drawings

2-O-PYRIMIDINYL GLYCEROL DERIVATIVES

FIELD OF INDUSTRIAL APPLICATION

This invention relates to glycerol derivatives useful as medicines. More particularly, this invention relates to compounds useful as antitumor agents having the formula:

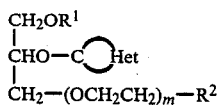  (I)

wherein

represents a nitrogen-containing aromatic 6-membered $R^1$ represents a higher alkyl group which may be substituted; $R^2$ represents a tertiary amino group or a quaternary ammonium group; and m represents 2 or 3 and salts thereof.

PRIOR ART

Recently it was disclosed that among amphipathic glycerolipids, those having certain structural elements showed antitumor activities. For example, there is known a phospholipid represented off the formula (II) [W. E. Berdel, W. R. E. Bausert, U. Fink, K. Rostetter and P. G. Munder, Anticancer Research, 1, 345(1981)]. However, this compound has also effects such as serotonin release, bronchoconstriction, platelet aggregation and hypotension, so that the clinical use of this compound is restricted due to side effects accompanied by the above-mentioned activities.

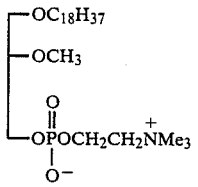 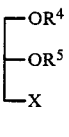

Recently it was disclosed that glycerolipids having no phosphate group (III) ($R^4$=a long chain alkyl, $R^5$=a short or long chain alkyl or acyl having 2 to 5 carbon atoms, X=O(CH$_2$)m-Y, m=1 to 12, Y=amino, acylamino, dialkylamino or quaternary ammonium) showed platelet-activating factor (PAF) antagonism and might be used as therapeutic agents for PAF-related disorders such as anaphylactic shock [Japanese Unexamined Patent Publication No. 100544/1985; Japanese Unexamined Patent Publication No. 198445/1983 (which respectively correspond to EP-A No. 142333 and EP-A- No. 94586); T. Miyamoto et al., Kyoto Conference of Prostaglandins, Nov. 26–28, 1984, Abst. p99]. However, improvement in duration of the effect and in therapeutic index is required for practical use of the compounds. There has been no concrete disclosure of antitumor activity about the compounds.

Currently, it is expected that it will be shown that abnormal proliferation of carcinoma cells is derived from structural and functional abnormalities of membranes of carcinoma cells. It has also been gradually clarified that amphipathic lipids have affinity for membranes of cells and therefore may exert various influences on cellular metabolism and functions through the membranes.

The present inventors supposed that among amphipathic lipids there might exist those having high selectivity to carcinoma cells and useful as carcinostatic agents. Prior studies have revealed that carcinoma cells are generally inferior to normal cells in cleaving an alkyl ether group [Wykle, R. L. and Snyder, F., The Enzymes of Biological Membranes, Martonosi, A., Ed., Vol. 2, Plenum Press, New York, 1976, 87; Lin, H. J., Ho, F. C. S., and Lee, C. L. H., Cancer Res., 38, 946(1978); Modolell, M., Andreesen, R., Pahlke, W., Brugger, U., and Munder, P. G., Cancer Res., 39, 4681(1979)].

If these statements are true, it will be expected that alkyl ether compounds having certain structural elements may be accumulated more in carcinoma cells where metabolism proceeds more slowly, showing selective cytocidal activities.

As a result of the researches on various ether-type derivatives of glycerol, the present inventors have found that compounds represented by the formula (I) have antitumor activities including differentiation-inducing activity against various tumor cells, completing the present invention.

DISCLOSURE OF THE INVENTION

The present invention provides compounds represented by the above-mentioned formula (I) and salts thereof In the above-mentioned formula (I), the nitrogen-containing aromatic 6-membered ring represented by

includes aromatic 6-membered rings containing 1 to 3 nitrogen atoms such as pyridyl (2-pyridyl, 3-pyridyl, 4-pyridyl), pyrazinyl (2-pyrazinyl, 3-pyrazinyl), pyrimidinyl (2-pyrimidinyl, 4-pyrimidinyl, 5-pyrimidinyl), pyridazinyl (3-pyridazinyl, 4-pyridazinyl) and triazinyl (1,3,5-triazin-2-yl, etc.) The nitrogen-containing aromatic 6-membered ring may have a substituent such as halogen (e.g. fluorine, bromine, chlorine), lower ($C_{1-6}$) alkyl (e.g. methyl, ethyl, propyl, butyl), lower ($C_{1-6}$) alkylthio, N-lower ($C_{1-6}$) alkylamino, N,N-di-lower ($C_{1-6}$) alkylamino, lower ($C_{1-6}$) alkoxy, hydroxy, hydroxy-lower ($C_{1-6}$) alkyl (e.g. hydroxyethyl), amino-lower (C1-6) alkyl (e.g. aminoethyl), carbamoyl or ureido.

The higher alkyl group represented by $R^1$ includes alkyl groups having 10 to 20 carbon atoms such as n-decyl, n-undecyl, n-dodecyl, n-tetradecyl, n-hexadecyl, n-octadecyl and n-icosyl. The higher alkyl group may have a substituent such as cycloalkyl or halogen. The cycloalkyl group includes 3 to 8-membered cycloalkyl groups such as cyclopentyl and cyclohexyl. The halogen as a substituent to the above-mentioned higher alkyl group includes fluorine, bromine and chlorine. When $R^1$ is a substituted higher alkyl group, the position of substitution may be any substitutive position of the higher alkyl group, but the ω (omega) position is preferable. The substituted higher alkyl group includes 13- cyclopentyltridecyl, 10-cyclohexyldecyl, 12-cyclohexyldodecyl, 16,16,16-trifluorohexadecyl, 18,18,18-trifluorooctadecyl, 14,14,15,15,16,16,16-heptafluorohexadecyl, 16,16,17,17,18,18,18-heptafluorooctadecyl The tertiary amino group represented by $R^2$ includes a group represented by the formula:

wherein $R^3$ and $R^4$ independently represent a lower alkyl group, or form a cyclic amino group taken together with the adjacent nitrogen atom, and a heterocyclic group containing a tertiary nitrogen atom.

The quaternary ammonium group represented by $R^2$ includes a group represented by the formula:

wherein $R^3$, $R^4$ and $R^5$ independently represent a lower alkyl group, or form a cyclic ammonium group taken together with the adjacent nitrogen atom, and a heterocyclic group containing a quaternary nitrogen atom.

The lower alkyl group represented by $R^3$, $R^4$ or $R^5$ includes alkyl groups having 1 to 6 carbon atoms such as methyl, ethyl, propyl, butyl and pentyl, among which a methyl group is preferable.

The cyclic amino group which $R^3$ and $R^4$ form taken together with the adjacent nitrogen atom includes 1-pyrrolidinyl, piperidino, morpholino and 1-piperazinyl, and these groups may have a substituent such as lower ($C_{1-6}$) alkyl (e.g. methyl, ethyl, propyl, butyl), carboxy, lower ($C_{1-6}$) alkoxycarbonyl, mercapto, hydroxy, hydroxy-lower ($C_{1-6}$) alkyl, amino-lower ($C_{1-6}$) alkyl, carbamoyl or ureido.

The cyclic ammonium group which $R^3$, $R^4$ and $R^5$ form taken together with the adjacent nitrogen atom includes 1-pyridinio, 3-oxazolio, 3-thiazolio, 1-[lower ($C_{1-6}$) alkyl]-3-imidazolio, 1-pyrimidinio, 1-pyridazinio, 1-quinolinio, 2-isoquinolinio, 1-[lower ($C_{1-6}$) alkyl]-1-pyrrolidinio, 1-[lower ($C_{1-6}$) alkyl]-1-piperidinio, 4-[lower ($C_{1-6}$) alkyl]-4-morpholinio and 1-[lower ($C_{1-6}$) alkyl]-1-piperazinio, and these groups may further have a substituent such as lower ($C_{1-6}$) alkyl, carboxy, lower ($C_{1-6}$) alkoxycarbonyl, mercapto, hydroxy, hydroxy-lower ($C_{1-6}$) alkyl, amino-lower ($C_{1-6}$) alkyl, carbamoyl or ureido.

The heterocyclic group containing a tertiary nitrogen atom represented by $R^2$ includes 1-[lower ($C_{1-6}$) alkyl]-pyrrolidin-2- or -3-yl, 1-[lower ($C_{1-6}$) alkyl]piperidin-2-, -3- or -4-yl, 4-[lower ($C_{1-6}$) alkyl]morpholin-2- or -3-yl and 1-[lower ($C_{1-6}$) alkyl]piperazin-2- or -3-yl, and these groups may have a substituent such as lower ($C_{1-6}$) alkyl, carboxy, lower ($C_{1-6}$) alkoxycarbonyl, mercapto, hydroxy, hydroxy-lower ($C_{1-6}$) alkyl, amino-lower ($C_{1-6}$) alkyl, carbamoyl or ureido.

The heterocyclic group containing a quaternary nitrogen atom represented by $R^2$ includes 1-[lower ($C_{1-6}$) alkyl]-2-, -3- or -4-pyridinio, 3-[lower ($C_{1-6}$) alkyl]-2-, -4- or -5-oxazolio, 3-[lower ($C_{1-6}$) alkyl]-2-, -4- or -5-thiazolio, 1-[lower ($C_{1-6}$) alkyl]-2-, -3-, -4-, -5-, -6-, -7- or -8-quinolinio, 2-[lower ($C_{1-6}$) alkyl]-1-, -3-, -4-, -5-, -6-, -7- or -8-isoquinolinio, 1,1-di[lower ($C_{1-6}$) alkyl]-2- or -3-pyrrolidinio, 1,1-di[lower ($C_{1-6}$) alkyl]-2-, -3- or -4-piperidinio, 4,4-di[lower ($C_{1-6}$) alkyl]-2- or -3-morpholinio and 1,1,4-tri[lower ($C_{1-6}$) alkyl]-2- or -3-piperazinio, and these groups may further have a substituent such as lower ($C_{1-6}$) alkyl, carboxy, lower ($C_{1-6}$) alkoxycarbonyl, mercapto, hydroxy, hydroxy-lower ($C_{1-6}$) alkyl, amino-lower ($C_{1-6}$) alkyl, carbamoyl or ureido.

m represents 2 or 3, among which 2 is preferable.

When $R^2$ is a tertiary amino group, the compounds (I) may form pharmaceutically acceptable salts with an inorganic acid such as hydrochloric acid, hydrobromic acid, hydroiodic acid or sulfuric acid or with an organic acid such as acetic acid, lactic acid, tartaric acid, citric acid, methanesulfonic acid, ethanesulfonic acid, benzenesulfonic acid or toluenesulfonic acid.

When $R^2$ is a quaternary ammonium group, the compounds (I) may form salts with an anion ($W^-$) or may form intramolecular salts with an anion in the molecule.

The anion in the molecule includes oxido (hydroxy), sulfido (mercapto) and carboxylato (carboxy).

The anion as $W^-$ when $R^2$ is a quaternary ammonium group includes pharmaceutically acceptable anions such as anions of inorganic acids (e.g. hydrochloric acid, hydrobromic acid, hydroiodic acid, sulfuric acid) and anions of organic acids (e.g. acetic acid, lactic acid, tartaric acid, citric acid, methanesulfonic acid, ethanesulfonic acid, benzenesulfonic acid, toluenesulfonic acid), among which halogen ions (e.g. chloride ion, bromide ion, iodide ion) are preferable.

Because the carbon atom at the 2-position of glycerol in the compounds represented by the formula (I) is an asymmetric center, there are two stereoisomers having R-configuration and S-configuration, but each isomer, a racemate and a mixture thereof are all included in the present invention.

The compound (I) of the present invention can be produced, for example, by the following procedures.

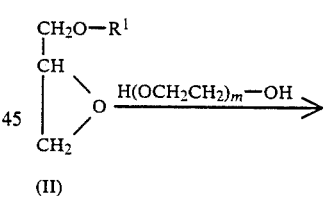

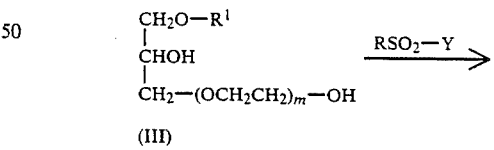

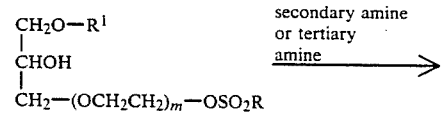

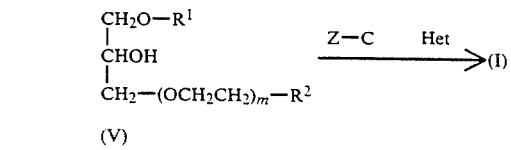

In the schema, $R^1$, $R^2$ and m have the same meanings as above, Y and Z independently represent halogen, and R represents phenyl, tolyl or lower ($C_{1-6}$) alkyl.

The glycidyl ether (II) is produced from an alcohol ($R^1OH$) in accordance with conventional methods, and the product is further reacted with a dialcohol [$H(OCH_2CH_2)_m$—OH] in accordance with conventional methods, to give the compound (III).

The compound (IV) can be produced by subjecting the compound (III) and a sulfonyl halide ($RSO_2$—Y) in an amount of 0.8 to 1.1 equivalent, preferably 0.85 to 1.00 equivalent, per equivalent of the compound (III), to a reaction in an appropriate anhydrous solvent (e.g. benzene, toluene, dichloromethane, chloroform, etc. or a mixture thereof) in the presence of an appropriate base (e.g. a tertiary amine such as triethylamine or pyridine) at $-50°$ to $+40°$ C., preferably $-30°$ to $+30°$ C., for 0.5 to 10 hours, preferably 1 to 3 hours.

The compound (V) can be produced by subjecting the compound (IV) and an excess amount of a secondary amine

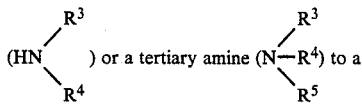

reaction as they are or in an appropriate solvent (e.g. water, methanol, ethanol, benzene, toluene, tetrahydrofuran, dimethylformamide, etc. or a mixture thereof) at $-20°$ to $+150°$ C., preferably $0°$ to $+80°$ C. When necessary, the reaction can be carried out at an ordinary temperature or with heating in a sealed tube to produce it. When the compound (V) is obtained in the form of a salt and ion exchange is necessary, the desired salt may be obtained by ion exchange chromatography, etc.

The compound (I) can be produced by reacting the compound (V) and

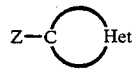

using 1 to 5 equivalents, preferably 1.5 to 3 equivalents, per equivalent of the compound (V) in the presence of a strong base [e.g. an excess of 10 to 50%, preferably 30 to 50%, aqueous sodium hydroxide solution] in an appropriate solvent (e.g. dichloromethane, tetrahydrofuran, dioxane, toluene, etc. or a mixture thereof) at $-10°$ to $+80°$ C., preferably $+10°$ to $+40°$ C., for 1 to 100 hours, preferably 4 to 24 hours. When necessary, the reaction may be carried out by using a phase-transfer catalyst (e.g. cetyltrimethylammonium chloride) of 0.01 to 0.2 equivalent, preferably 0.02 to 0.05 equivalent, per equivalent of the compound (V).

The compound (V) can also be obtained by reacting the compound (II) with an aminoalcohol [$H(OCH_2CH_2)_m$—$R^2$].

The compound (I) of the present invention can also be produced by, for example, the following procedures.

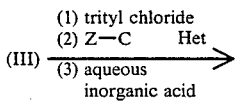

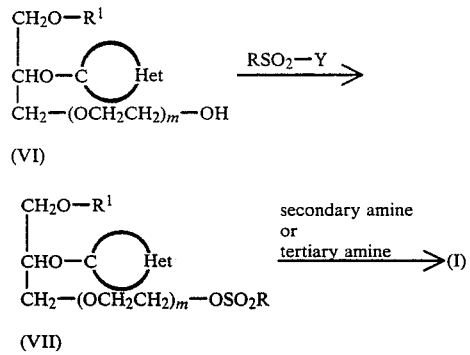

In the schema, each of the symbols has the same meaning as above.

The reaction of (III)→(VI) is carried out by reacting the compound (III) with trityl chloride to protect the primary alcohol group, and reacting the obtained trityl ether derivative with

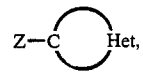

and then removing the trityl group by an aqueous inorganic acid.

The reactions of (VI)→(VII) and (VII)→(I) can be carried out under the same conditions as those of (III)→(IV) and (IV)→(V), respectively. The compound of the formula (I) wherein $R^2$ is a quaternary ammonium group can also be produced by reacting the compound of the formula (I) wherein $R^2$ is a tertiary amino group with a lower ($C_{1-6}$) alkyl halide (Y—$R^5$) or a lower ($C_{1-6}$) alkyl sulfonate ($RSO_2$—O—$R^5$). This procedure is generally carried out in a solvent (e.g. ether, chloroform, tetrahydrofuran, benzene, toluene) at $0°$ to $+100°$ C.

When $R^2$ is a tertiary amino group, a salt of the compound (I) may be obtained by the methods for producing the compound (I), but the salt can also be produced by addition of an inorganic acid or organic acid, when necessary.

When $R^2$ is a quaternary ammonium group, $W^-$ can also be exchanged with another anion by an ion exchange resin.

Representative methods for production of the compound (I) are described above, but the methods for production of the compound (I) should not be limited only to those.

The compounds (I) are found to have substantially no platelet aggregation activity, hypotensive activity and vessel permeability-enhancing activity. The compounds (I) show increased efficacy and prolonged duration with respect to the main actions (e.g. antitumor activities including differentiation-inducing activity).

Thus, the compounds prolong the life span of cancer-bearing mice inoculated with murine sarcoma S180 and murine breast cancer MM46 cells, and further inhibit remarkably the proliferation of human promyelocytic leukemia HL-60 cells and human non-small cellular lung cancer HUT29 and A549 cells which are considered to be highly resistant to drugs. Therefore, the compounds (I) and salts thereof can be administered to cancer-bearing warm-blooded animals as safe antitumor agents. Schedule, route and dosage of the administration can be appropriately chosen according to the subjects to be administered and the symptoms to be treated, but the dose for a mammal is usually about 0.1 to 150 mg/kg body weight, preferably 2 to 50 mg/kg body weight, on the compound (I) basis. Frequency of administration of the drug is about 1 to 3 times a day, or at the intervals of 2 to 7 days. The compound can also be administered by intravenous drip infusion over long time to maintain the level of the compound in tissues at a required level over a long period. In parenteral administration of the compound, combination with serum albumin or various globulins is expected to further improve the safety, for example by preventing tissue (local) impairment without affecting the efficacy.

The compounds (I) and their salts are excellent both in hydrophilic and lipophilic properties, and therefore can be safely administered orally or parenterally to mammals as powder as they are or as a pharmaceutical composition in a suitable dosage form.

Pharmaceutical compositions used for administration contain an effective amount of the compound (I) or a salt thereof and a pharmaceutically acceptable carrier or excipient.

Injections for parenteral administration by the present invention include sterilized aqueous or non-aqueous solutions, suspensions or emulsions. Aqueous solutions and suspensions include, for example, distilled water and physiological saline. Non-aqueous solutions and suspensions include intralipid, propylene glycol, polyethylene glycol, vegetable oils such as olive oil, alcohols such as ethanol, and polysorbate 80. Such compositions may contain additionally supplements such as antiseptics, moistening agents, emulsifiers and dispersants, and aqueous injections may contain supplements such as glucose, serum albumin and serum (plasma) globulins. These compositions are sterilized by filtration through bacterial filter, by combination of disinfectants or by ultraviolet ray irradiation. Sterilized solid compositions are also produced and then dissolved in sterilized water or sterilized solvent for injection before use. Tablets and capsules can be prepared in accordance with conventional methods. To prepare these solid compositions, the compound (I) or a salt thereof is mixed with at least one inactive carrier or excipient such as lactose, mannitol, glucose, hydroxypropylcellulose, microcrystalline cellulose or starch. The compositions may contain an additive other than inactive carrier or excipient, for example, a lubricant such as magnesium stearate or a disintegrator such as calcium cellulose gluconate.

The present invention is illustrated in more detail by Reference Examples, Examples and Test Examples in the following, but this invention should not be limited to those.

REFERENCE EXAMPLE 1

2-[2-[(2-Hydroxy-3-octadecyloxy)propoxy]ethoxy]ethanol

Epichlorohydrin [55.5 g (0.6 mole)] was dissolved in toluene (100 ml), to which were added stearyl alcohol [40.7 g (0.15 mole)], cetyltrimethylammonium chloride [2.4 g (7.5 millimoles)] and 50% sodium hydroxide (56 g), and then the resulting mixture was stirred at 60° C. for 3 hours.

After cooling, hexane (500 ml) was added to the mixture and insoluble materials were removed by filtration, and then the material having a low boiling point was evaporated off under reduced pressure Hexane (400 ml) was added to the residue, and insoluble materials were removed by filtration, and then hexane was evaporated off under reduced pressure.

The residue was dissolved in a mixture of dioxane (1 l) and diethyleneglycol (300 g), and 60% oily sodium hydride [2 g (0.05 mole)] was added to the mixture. The resulting mixture was stirred at room temperature for 10 minutes and then stirred at 110° C. for 5 hours. Dioxane was evaporated off under reduced pressure, and saline and a mixture of hexane and ether (1:1) were added to the residue, and then the mixture was shaken for separation into layers.

The upper layer collected was concentrated under reduced pressure, and the residue was purified by silica gel column chromatography [Merck, Art. 7734, 600 g (eluent: hexane-ethyl acetate-acetone=5:1:1–2:1:1)] to give the above-identified compound [36.8 g (57%)].

IR (Neat) cm$^{-1}$: 3440, 2920, 2855, 1465, 1120, 1070.

NMR (90 MHz, CDCl$_3$) δ: 0.87 (3H), 1.27 (32H), 2.57 (2H), 3.40–3.80 (14H), 3.97 (1H).

REFERENCE EXAMPLE 2

N-2-[2-[(2-Hydroxy-3-octadecyloxy)propoxy]ethoxy]ethyl-N,N,N-trimethylammonium chloride 2-[2-[(2-Hydroxy-3-octadecyloxy)propoxy]ethoxy]ethanol [18.4 g (42.5 millimoles)] obtained in Reference Example 1 was dissolved in dichloromethane (190 ml). To the mixture with stirring under ice-cooling, triethylamine [4.5 g (45 millimoles)] was added and then methanesulfonyl chloride [5 g (43 millimoles)] was added dropwise for a period of 1 hour. The resulting mixture was stirred for 1 hour under ice-cooling, and then washed with dilute hydrochloric acid and aqueous sodium hydrogencarbonate solution. Dichloromethane was evaporated off and the residue was dissolved in a mixture of tetrahydrofuran (40 ml) and ethanol (200 ml). To the mixture was added 30% aqueous trimethylamine (20 ml), and the resulting mixture was heated at 75° C. for 15 hours in a 300 ml-stainless tube, and then evaporated to dryness under reduced pressure. The residue was allowed to pass through a column of Amberlite ® IRA-410 [Cl$^-$] (100 ml; eluent: methanol), and methanol was evaporated off under reduced pressure. The residue was purified by silica gel column chromatography [Merck, Art. 7734, 300 g (eluent: chloroform-methanol=10:1–3:1, chloroform-methanol-water=65:25:1–65:25:4)], to give the above-identified compound [12.0 g (54%)].

IR (CHCl$_3$) cm$^{-1}$: 3400, 2930, 2860, 1465, 1185, 1110, 1010.

NMR (90 MHz, CDCl$_3$) δ: 0.87 (3H), 1.27 (32H), 2.60 (3H), 3.40–4.17 (24H).

REFERENCE EXAMPLE 3

2-[2-[3-Octadecyloxy-2-(pyrimidin-2-yloxy)propoxy]ethoxy]ethyl methanesulfonate

2-[2-[(2-Hydroxy-3-octadecyloxy)propoxy]ethoxy] ethanol [43 g (0.1 mole)] obtained in Reference Example 1 was dissolved in pyridine (150 ml), to which was added trityl chloride [42 g (0.15 mole)], and then the resulting mixture was stirred at 80° C. for 2 hours. Methanol (1 ml) was added to the mixture and the whole mixture was stirred at the same temperature for 0.5 hour, and then pyridine was evaporated off under reduced pressure.

The residue was extracted with ether and ether was evaporated off. The residue was purified by silica gel column chromotography [Merck, Art. 7734, 1 kg (eluent: hexane-ethyl acetate=10:3–3:1)] to give 2-[2-[(2-hydroxy-3-octadecyloxy)propoxy]ethoxy]ethyl trityl ether.

This product was dissolved in tetrahydrofuran (300 ml), to which was added 2-chloropyrimidine [22 g (0.2 mole)], and then 60% oily sodium hydride [8 g (0.2 mole)] was added to the mixture with stirring at about 20° C. for a period of 30 minutes.

The mixture was then stirred at 50° C. on an oil bath for 15 hours, and tetrahydrofuran was evaporated off under reduced pressure. Ether (500 ml) was added to the residue, and water (10 ml) was added to the mixture for a period of 15 minutes with stirring at room temperature and then water (150 ml) was further added The mixture was shaken and the ether layer was collected by separation.

Ether was evaporated off and the residue was dissolved in a mixture of methanol (50 ml) and tetrahydrofuran (100 ml), and then conc. hydrochloric acid (5 ml) was added to the mixture. After the mixture was allowed to stand at room temperature for 4 hours, an aqueous solution (100 ml) of anhydrous potassium carbonate (9 g) was added to the mixture, and then the organic solvents were evaporated off under reduced pressure.

The remaining oil was extracted with ether, and ether was evaporated off. The residue was purified by silica gel column chromatogaphy [Merck, Art. 7734, 700 g (eluent: hexane-ethyl acetate-acetone=2:1:1–1:1:1)] to give 2-[2-[3-octadecyloxy-2-(pyrimidin-2-yloxy)-propoxy]ethoxy]ethanol. This product was dissolved in dichloromethane (200 ml), and trimethylamine [20 g (0.2 mole)] was further added. Methanesulfonyl chloride [15 g (0.13 mole)] was added to the mixture with stirring under ice-cooling, and then the resulting mixture was stirred for 1 hour under the same conditions. Further, water (20 ml) was added and the mixture was stirred for 0.5 hour. The mixture was washed with dilute hydrochloric acid and aqueous sodium hydrogencarbonate solution successively, and dichloromethane was evaporated off to give the above-identified compound [47 g (80%)].

IR (Nujol) cm$^{-1}$: 1575, 1565, 1420, 1375, 1340, 1165, 1115.

NMR (90 MHz, CDCl$_3$) δ: 0.87 (3H), 1.27 (32H), 3.03 (3H), 3.43 (2H), 3.63–3.80 (10H), 4.33 (2H), 5.50 (1H), 6.97 (1H), 8.57 (2H).

REFERENCE EXAMPLE 4

2-[2-[(2-Hydroxy-3-octadecyloxy)propoxy]ethoxy]ethyl triphenylmethyl ether

2-[2-[(2-Hydroxy-3-octadecyloxy)propoxy]ethoxy]ethanol [43.3 g (0.1 mole)] obtained in Reference Example 1 was dissolved in pyridine (200 ml), to which triphenylchloromethane (42 g (0.15 mole)] was added, and then the mixture was stirred at 80° C. for 3 hours. Methanol (20 ml) was added to the mixture, and the reaction mixture was stirred for 0.5 hour under the same conditions. After cooling, the reaction mixture was concentrated under reduced pressure. Water (500 ml) and a mixture of ethyl acetate and hexane (1:1; 600 ml) were added to the residue, and the resulting mixture was shaken for separation into layers. The upper layer collected was washed with water (300 ml) and concentrated under reduced pressure. The residue was purified by silica gel column chromatography [Merck, Art. 7734, 800 g (eluent: hexane-ethyl acetate=6:1–3:1)] to give the above-identified compound [42 g (62%)].

IR (Neat) cm$^{-1}$: 3420, 2920, 2850, 1490, 1465, 1445, 1110, 1085, 755, 705.

NMR (90 MHz, CDCl$_3$) δ: 0.87 (3H), 1.23 (32H), 2.60 (1H), 3.17–3.70 (14H), 3.80–4.10 (1H), 7.20–7.60 (15H).

REFERENCE EXAMPLE 5

2-[2-[2-[(2-Methylthiopyrimidin-4-yloxy)-3-octadecyloxy]propoxy]ethoxy]ethanol

2-[2-[(2-Hydroxy-3-octadecyloxy)propoxy]ethoxy]ethyl triphenylmethyl ether [15.5 g (23 millimoles)] obtained in Reference Example 4 was dissolved in tetrahydrofuran (30 ml), and then 4-chloro-2-methylthiopyrimidine [7.4 g (46 millimoles)] was added to the mixture. Sixty (60)% oily sodium hydride [1.8 g (46 millimoles)] was added to the mixture with stirring at room temperature, and the resulting mixture was stirred at 50° C. for 2.5 hours. The reaction mixture was transferred to an ice bath, and ethanol (10 ml) was added to the mixture to decompose the unreacted sodium hydride, and then materials having a low boiling point were evaporated off under reduced pressure. Water (50 ml) and a mixture of hexane and ether (2:1; 150 ml) were added to the residue, and the resulting mixture was shaken for separation into layers. The upper layer collected was concentrated under reduced pressure. The residue was dissolved in a mixture of tetrahydrofuran and methanol (1:1), to which conc. hydrochloric acid (10 ml) was added, and then the mixture was allowed to stand at room temperature for 3 hours. The mixture was made alkaline with anhydrous potassium carbonate (20 g) in water (150 ml), and then the organic solvents were evaporated off under reduced pressure. The residue was extracted with ether and the extract was concentrated under reduced pressure, and then the residue was purified by silica gel column chromatography [Merck, Art. 7734, 200 g (eluent: hexane-ethyl acetate-acetone=8:1:1–3:1:1)] to give the above-identified compound [12.7 g (99%)].

IR (Nujol) cm$^{-1}$: 3475, 1570, 1555, 1445, 1315, 1225, 1120.

NMR (90 MHz, CDCl$_3$) δ: 0.87 (3H), 1.27 (32H), 2.50 (3H), 3.37–3.80 (14H), 5.53 (1H), 6.43 (1H), 8.23 (1H).

REFERENCE EXAMPLE 6

2-[2-[3-Octadecyloxy-2-(pyrimidin-4-yloxy)propoxy]ethoxy]ethanol

2-[2-[2-[(2-Methylthiopyrimidin-4-yloxy)-3-octadecyloxy]propoxy]ethoxy]ethanol [9.3 g (16.7 millimoles)] was dissolved in ethanol (120 ml), to which Raney Nickel [NDHT-90® (Kawaken Fine Chemical); 30 g] was added, and the mixture was stirred at 70° C. for 2 hours. The catalyst was separated by filtration and washed with warm ethanol. The filtrate and washings were combined and ethanol was evaporated off under reduced pressure to give the above-identified compound [6.1 g (72%)].

IR (Neat) cm$^{-1}$: 3400, 2920, 2855, 1585, 1560, 1465, 1390, 1300, 1115, 1070, 990.

NMR (90 MHz, CDCl$_3$) δ: 0.87 (3H), 1.27 (32H), 2.00 (1H), 3.37–3.80 (14H), 5.60 (1H), 6.77 (1H), 8.43 (1H), 8.77 (1H).

REFERENCE EXAMPLE 7

2-[2-[3-Octadecyloxy-2-(pyrimidin-4-yloxy)propoxy]ethoxy]ethyl methanesulfonate

2-[2-[3-Octadecyloxy-2-(pyrimidin-4-yloxy)propoxy]ethoxy]ethanol [6.1 g (11.9 millimoles)] obtained in Reference Example 6 was subjected to a methanesulfonation reaction in the same manner as that of Reference Example 3, to give the above-identified compound [7 g (quantitative)].

IR (Nujol) cm$^{-1}$: 1585, 1575, 1345, 1295, 1170, 1115.

NMR (90 MHz, CDCl$_3$) δ: 0.87 (3H), 1.27 (32H), 3.03 (3H), 3.43 (2H), 3.63–3.83 (10H), 4.30 (2H), 5.57 (1H), 6.77 (1H), 8.47 (1H), 8.77 (1H).

REFERENCE EXAMPLE 8

2-[2-[2-[(2-Hydroxy-3-octadecyloxy)propoxy]ethoxy]ethoxy]ethyl triphenylmethyl ether 2,3-Epoxy-3-octadecyloxypropane [10.1 g (31 millimoles)] obtained as an intermediate in Reference Example 1 was dissolved in dioxane (200 ml), and triethylene glycol [93 g (630 millimoles)] was added to the mixture. Sixty (60)% oily sodium hydride [400 mg (10 millimoles)] was added to the mixture with stirring at 50° C., and the resulting mixture was stirred for 10 minutes under the same conditions. The mixture was further stirred at 110° C. for 4 hours, and then cooled. Acetic acid (1 ml) was added to the mixture and then dioxane was evaporated off under reduced pressure. Water (600 ml) and a mixture of ether and hexane (4:1; 800 ml) were added to the residue, and the resulting mixture was shaken for separation into layers. The upper layer collected was dried over anhydrous magnesium sulfate and then the solvents were evaporated off under reduced pressure. The residue was dissolved in pyridine (60 ml), to which triphenylchloromethane [14 g (50 millimoles)] was added, and then the resulting mixture was stirred at 55° C. for 15 hours. Methanol (10 ml) was further added to the mixture and the mixture was stirred for 1 hour under the same conditions. Pyridine was evaporated off under reduced pressure, and then 20% saline (300 ml) and a mixture of hexane and ethyl acetate (4:1; 600 ml) were added to the residue. The resulting mixture was shaken for separation into layers, and the upper layer was concentrated and purified by silica gel column chromatography [Merck, Art. 7734, 250 g (eluent: hexane-ethyl acetate=4:1–2:1)] to give the above-identified compound [12.2 g (55%)].

IR (Neat) cm$^{-1}$: 3450, 2925, 2860, 1490, 1465, 1445, 1130, 1110, 1090, 1030, 1010, 770, 760, 745, 705.

NMR (90 MHz, CDCl$_3$) δ: 0.87 (3H), 1.27 (32H), 2.67 (1H), 3.23 (2H), 3.33–4.07 (17H), 7.20–7.53 (15H).

REFERENCE EXAMPLE 9

2-[2-[2-[3-Octadecyloxy-2-(pyrimidin-2-yloxy)propoxy]ethoxy]ethoxy]ethanol

2-[2-[2-[(2-Hydroxy-3-octadecyloxy)propoxy]ethoxy]ethoxy]ethyl triphenylmethyl ether [7.2 g (10 millimoles)] obtained in Reference Example 8 was reacted with 2-chloropyrimidine [2.3 g (20 millimoles)] in the same manner as that of Reference Example 5 to give the above-identified compound [4.9 g (92%)].

IR (Neat) cm$^{-1}$: 3400, 2920, 2855, 1575, 1560, 1465, 1420, 1320, 1115, 1070.

NMR (90 MHz, CDCl$_3$) δ: 0.87 (3H), 1.27 (32H), 2.60 (1H), 3.47 (2H), 3.60–3.83 (16H), 5.47 (1H), 6.90 (1H), 8.47 (2H).

REFERENCE EXAMPLE 10

2-[2-[2-[3-Octadecyloxy-2-(pyrimidin-2-yloxy)propoxy]ethoxy]ethoxy]ethyl methanesulfonate 2-[2-[2-[3-Octadecyloxy-2-(pyrimidin-2-yloxy)propoxy]ethoxy]ethoxy]ethanol [4.9 g (9.3 millimoles)] obtained in Reference Example 9 was subjected to the same reaction as that in Reference Example 7, to give the above-identified compound [5.6 g (quantitative)].

IR (Neat) cm$^{-1}$: 2920, 2855, 1575, 1565, 1465, 1420, 1345 1325, 1170, 1105, 1015.

NMR (90 MHz, CDCl$_3$) δ: 0.87 (3H), 1.27 (32H), 3.07 (3H), 3.47 (2H), 3.60–3.83 (14H), 4.30–4.43 (2H), 5.47 (1H), 6.90 (1H), 8.47 (2H).

EXAMPLE 1

N-2-[2-[3-Octadecyloxy-2-(pyrimidin-2-yloxy)propoxy]ethoxy]ethyl-N,N,N-trimethylammonium chloride 2-Chloropyrimidine (2.3 g (20 millimoles)] was dissolved in a mixture of dichloromethane (20 ml) and tetrahydrofuran (25 ml), to which N-2-[2-[(2-hydroxy-3-octadecyloxy)propoxy]ethoxy]ethyl-N,N,N-trimethylammonium chloride [3.7 g (7 millimoles)] obtained in Reference Example 2 and 50% sodium hydroxide (4.8 g) were added, and then the resulting mixture was stirred at room temperature for 60 hours. The organic solvents were evaporated off under reduced pressure, and 6N hydrochloric acid was added to the residue to adjust the pH to 3. The mixture was extracted with dichloromethane, and the dichloromethane layers were combined and evaporated. The residue was purified by silica gel column chromatography [Merck, Art. 7734, 120 g (eluent: chloroform-methanol=9:1–65:25 chloroform-methanol-water=65:25:1–65:25:4)] to give the above-identified compound [3 g (67%)].

IR (Nujol) cm$^{-1}$: 3350, 1570, 1420 1330, 1130, 1110.

NMR (90 MHz, CDCl$_3$) δ: 0.87 (3H), 1.27 (32H), 3.33–4.10 (23H), 5.43 (1H), 6.97 (1H), 8.53 (2H).

EXAMPLE 2

N-[2-[2-[2-(3-Chloropyridazine-6-yloxy)-3-octadecyloxy]propoxy]ethoxy]ethyl-N,N,N-trimethylammonium chloride 3,6-Dichloropyridazine (1.2 g (8 millimoles)] was dissolved in 12 ml of toluene, to which N-2-[2-[(2-hydroxy-3-octadecyloxy)propoxy]ethoxy]ethyl-N,N,N-trimethylammonium chloride [2.6 g (4 millimoles)] obtained in Reference Example 2 and 50% sodium hydroxide (1 g) were added, and then the resulting mixture was stirred at room temperature for 6 hours. Toluene (100 ml) was added to the mixture and materials insoluble in toluene were removed by filtration and then toluene was evaporated off under reduced pressure. The residue was dissolved in methanol and then allowed to pass through a column of Amberlite ® IRA-410 [Cl$^-$] (100 ml; eluent: methanol). Methanol was evaporated off under reduced pressure and the residue was purified by silica gel column chromatography [Merck, Art. 7734, 60 g (eluent: chloroform-methanol=6:1–65:25, chloroform-methanol-water=65:25:1–65:25:4)] to give the above-identified compound [2.0 g (77%)].

IR (Neat) cm$^{-1}$: 3400, 2920, 2855, 1465, 1415, 1305, 1120.

NMR (90 MHz, CDCl$_3$-CD$_3$OD) δ: 0.87 (3H), 1.27 (32H), 3.27 (9H), 3.40–4.00 (14H), 5.63 (1H), 7.13 (1H), 7.50 (1H).

EXAMPLE 3

N-[2-[2-[3-Octadecyloxy-2-(pyridazin-3-yloxy)propoxy]ethoxy]ethyl]-N,N,N-trimethylammonium chloride N-[2-[2-[2-(3-Chloropyridazin-6-yloxy)-3-octadecyloxy]propoxy]ethoxy]ethyl-N,N,N-trimethylammonium chloride [510 mg (0.8 millimole)] obtained in Example 2 was dissolved in methanol (10 ml), to which 2N NaOH (0.4 ml) and 5% palladium-carbon powder (400 mg) were added, and then hydrogenolysis was carried out at room temperature under atmospheric pressure for 30 minutes. The catalyst was removed by filtration and then the solvent was evaporated off under reduced pressure.

The residue was purified by silica gel column chromatography [Merck, Art. 7734, 20 g (eluent: chloroform-methanol-water=65:25:3–65:25:4)] to give the above-identified compound [250 mg (53%)].

IR (Nujol) cm$^{-1}$: 3400, 1590, 1440, 1380, 1290, 1115.
NMR (90 MHz, CDCl$_3$-CD$_3$OD) δ: 0.87 (3H), 1.10–1.70 (32H), 3.27 (9H), 3.40–4.00 (14H), 5.70 (1H), 7.20 (1H), 7.53–7.60 (1H), 8.90 (1H).

EXAMPLE 4

3-[2-[2-[3-Octadecyloxy-2-(pyrimidin-2-yloxy)propoxy]ethoxy]ethyl]thiazolium chloride 2-[2-[3-Octadecyloxy-2-(pyrimidin-2-yloxy)propoxy]ethoxy]ethyl methanesulfonate [0.85 g (1.44 millimole)] obtained in Reference Example 3 was dissolved in thiazole (3 g), and the mixture was stirred at 80° C. for 27 hours.

Thiazole was evaporated off under reduced pressure and the residue was allowed to pass through a column of Amberlite® IRA-410 [Cl] (20 ml, eluent: methanol-water=10:1) for ion exchange. The solvents in the eluate were evaporated off and the residue was purified by silica gel column chromatography [Merck, Art. 7734, 30 g (eluent: chloroform-methanol=9:1, chloroform-methanol-water=65:15:2–65:25:4)] to give the above-identified compound [875 mg (99 %)].

IR (KBr) cm$^{-1}$: 3425, 2925, 2860, 1575, 1565, 1465, 1425, 1325, 1115.
NMR (90 MHz, CDCl$_3$) δ: 0.87 (3H), 1.13–1.67 (32H), 3.47 (2H), 3.60–3.80 (10H), 3.97 (2H), 5.17 (2H), 5.47 (1H), 7.00 (1H), 8.40 (1H), 8.57 (2H), 8.93 (1H), 11.63 (1H).

EXAMPLE 5

3-Carbamoyl-1-[2-[2-[3-octadecyloxy-2-(pyrimidin-2-yloxy)propoxy]ethoxy]ethyl]pyridinium chloride.

2-[2-[3-Octadecyloxy-2-(pyrimidin-2-yloxy)propoxy]ethoxy]ethyl methanesulfonate [2 g (3.4 millimoles)] obtained in Reference Example 5 and nicotinamide [1.2 g (10 millimoles)] were dissolved in dimethylformamide (10 ml), and the mixture was heated at 90° C. for 15 hours.

Dimethylformamide was evaporated off under reduced pressure and the residue was dissolved in dichloromethane (150 ml). Ethanol (5 ml) was added to the mixture and the resulting mixture was shaken with 25% saline (200 ml) for separation into layers.

The dichloromethane layer collected was concentrated and the residue was purified by silica gel column chromatography [Merck, Art. 7734, 60 g (eluent: chloroform-methanol-water=65:25:1–65:25:4)] to give the above-identified compound [1.1 g (50%)].

IR (Nujol) cm$^{-1}$: 3370, 3160, 3075, 1690, 1580, 1565, 1430, 1380, 1325, 1120.
NMR (90 MHz, CDCl$_3$—CD$_3$OD) δ: 0.87 (3H), 1.27 (32H), 3.40–3.80 (10H), 4.07 (2H), 4.93 (2H), 5.43 (1H), 7.00 (1H), 8.23 (1H), 8.53 (2H), 9.10 (2H), 10.17 (1H).

EXAMPLE 6

1-[2-[2-[3-Octadecyloxy-2-(pyrimidin-2-yloxy)propoxy]ethoxy]ethyl]pyridinio-3-carboxylate 2-[2-[3-Octadecyloxy-2-(pyrimidin-2-yloxy)propoxy]ethoxy]ethyl methanesulfonate [1.8 g (3 millimoles)] obtained in Reference Example 3 was dissolved in ethyl nicotinate [3.5 g (23 millimoles)], and the mixture was heated at 100° C. for 3 hours. The product was purified by silica gel column chromatography [Merck, Art. 7734, 50 g (eluent: chloroform-methanol-water=65:25:4)], and then dissolved in methanol (20 ml). Fifty (50)% sodium hydroxide (1 g) was added to the mixture and the resulting mixture was allowed to stand at room temperature for 15 hours. The pH of the mixture was adjusted to 3 with 2N hydrochloric acid and then methanol was evaporated off under reduced pressure. The residue was dissolved in dichloromethane (50 ml), and ethanol (5 ml) was added to the mixture. The mixture was shaken with 25% saline (50 ml) for separation into layers.

The dichloromethane layer collected was concentrated and the residue was purified by silica gel column chromatography [Merck, Art. 7734, 50 g (eluent: chloroform-methanol-water=65:25:4)] to give the above-identified compound [0.9 g (50%)].

IR (Nujol) cm$^{-1}$: 3460, 3250, 3055, 1635, 1610, 1580, 1565, 1425, 1380, 1120.
NMR (90 MHz, CDCl$_3$) δ: 0.87 (3H), 1.27 (32H), 3.30–3.80 (10H), 4.00 (2H), 5.00 (2H), 5.43 (1H), 6.97 (1H), 7.97 (1H), 8.53 (2H), 8.80–9.07 (2H), 9.77 (1H).

EXAMPLE 7

1-[2-[2-[3-Octadecyloxy-2-(pyrimidin-2-yloxy)propoxy]ethoxy]ethyl]pyridinio-4-carboxylate 2-[2-[3-Octadecyloxy-2-(pyrimidin-2-yloxy)propoxy]ethoxy]ethyl methanesulfonate [1.8 g (3 millimoles)] obtained in Reference Example 3 was reacted with ethyl isonicotinate (3.5 g) under the same conditions as those in Example 6 to give the above-identified compound [1.2 g (66%)].

IR (Nujol) cm$^{-1}$: 3420, 3125, 3050, 1630, 1565, 1420, 1360, 1325, 1120.
NMR (90 MHz, CDCl$_3$) δ: 0.87 (3H), 1.27 (32H), 3.37–3.80 (10H), 4.00 (2H), 4.90 (2H), 5.43 (1H), 6.93 (1H), 8.33 (2H), 8.50 (2H), 8.93 (2H).

EXAMPLE 8

4-t.-Butyl-1-[2-[2-[3-octadecyloxy-2-(pyrimidin-2-yloxy)propoxy]ethoxy]ethyl]pyridinium chloride 2-[2-[3-Octadecyloxy-2-(pyrimidin-2-yloxy)propoxy]ethoxy]ethyl methanesulfonate [884 mg (1.5 millimoles)] obtained in Reference Example 3 was reacted with 4-t.-butylpyridine (700 mg) under the same conditions as those in Example 5 to give the above-identified compound [900 mg (90%)].

IR (Nujol) cm$^{-1}$: 3400, 1640, 1575, 1565, 1420, 1375, 1330, 1310, 1110.
NMR (90 MHz, CDCl$_3$) δ: 0.87 (3H), 1.23 (32H), 1.40 (9H), 2.27 (1H), 3.43 (2H), 3.60–3.80 (8H), 4.00 (2H), 5.17 (2H), 5.47 (1H), 6.97 (1H), 8.07 (2H), 8.53 (2H), 9.60 (2H).

EXAMPLE 9

3-Hydroxy-1-[2-[2-[3-octadecyloxy-2-(pyrimidin-2-yloxy)propoxy]ethoxy]ethyl]pyridinium chloride 2-[2-[3-Octadecyloxy-2-(pyrimidin-2-yloxy)propoxy]ethoxy]ethyl methanesulfonate [1.2 g (2 millimoles)] obtained in Reference Example 3 was dissolved in 3-acetoxypyridine (1.5 g) and the mixture was heated at 100° C. for 4 hours.

This mixture was dissolved in methanol (10 ml), to which triethylamine (0.5 ml) was added, and then the resulting mixture was allowed to stand at room temperature for 15 hours.

Materials having a low boiling point were evaporated off under reduced pressure and the residue was dissolved in dichloromethane (100 ml), and the mixture was shaken with 30% saline (150 ml), of which the pH was adjusted to 2 with 2N hydrochloric acid, with addition of ethanol (10 ml) for separation. The dichloromethane layer collected was concentrated under reduced pressure and the residue was purified by silica gel column chromatography [Merck, Art. 7734, 25 g (eluent: chloroform-methanol=65:25)] to give the above-identified compound [770 mg (62%)].

IR (Nujol) cm$^{-1}$: 3330, 3060, 1575, 1565, 1510, 1425, 1380, 1325, 1315, 1110.

NMR (90 MHz, CDCl$_3$—CD$_3$OD) δ: 0.87 (3H), 1.27 (32H), 3.47 (2H), 3.60–3.80 (8H), 3.90 (2H), 4.53 (2H), 5.43 (1H), 6.97 (1H), 7.37–7.63 (2H), 7.80 (1H), 8.30 (1H), 8.53 (2H).

EXAMPLE 10

1-Methyl-3-[2-[2-[3-octadecyloxy-2-(pyrimidin-2-yloxy)propoxy]ethoxy]ethyl]imidazolium chloride 2-[2 [3-Octadecyloxy-2-(pyrimidin-2-yloxy)propoxy]ethoxy]ethyl methanesulfonate [550 mg (0.93 millimole)] obtained in Reference Example 3 was reacted with 1-methylimidazole (1 g) under the same conditions as those in Example 5 to give the above-identified compound [500 mg (86 %)].

IR (Neat) cm$^{-1}$: 3400, 1575, 1565, 1425, 1320, 1170, 1115.

NMR (90 MHz, CDCl$_3$) δ: 0.87 (3H), 1.23 (32H), 3.47 (2H), 3.63–3.93 (10H), 4.07 (3H), 4.60 (2H), 5.47 (1H), 6.97 (1H), 7.43 (1H), 7.77 (1H), 8.50 (2H), 10.37 (1H).

EXAMPLE 11

N-2-[2-[3-Octadecyloxy-2-(pyrimidin-4-yloxy)propoxy]ethoxy]ethyl-N,N,N-trimethylammonium chloride 2-[2-[3-Octadecyloxy-2-(pyrimidin-4-yloxy)propoxy]ethoxy]ethyl methanesulfonate [1.2 g (2.04 millimoles)] obtained in Reference Example 7 was dissolved in tetrahydrofuran (8 ml), to which 30% aqueous trimethylamine (3 ml) was added, and the mixture was allowed to stand at room temperature for 60 hours. The mixture was concentrated under reduced pressure, and the residue was dissolved in a mixture of dichloromethane and ethanol (95:5; 60 ml) and shaken with 30% saline (40 ml) for separation into layers. The lower layer collected was concentrated under reduced pressure and the residue was purified by silica gel column chromatography [Merck, Art. 7734, 40 g (eluent: chloroform-methanol-water=65:25:4)] to give the above-identified compound [673 mg (56%)].

IR (Nujol) cm$^{-1}$: 3390, 1640, 1585, 1305, 1115.

NMR (90 MHz, CDCl$_3$—CD$_3$OD) δ: 0.87 (3H), 1.23 (32H), 3.23 (9H), 3.43 (2H), 3.57–4.00 (12H), 5.60 (1H), 6.83 (1H), 8.47 (1H), 8.77 (1H).

EXAMPLE 12

3-Carbamoyl-1-[2-[2-[3-octadecyloxy-2-(pyrimidin-4-yloxy)propoxy]ethoxy]ethyl]pyridinium chloride 2-[2-[3-Octadecyloxy-2-(pyrimidin-4-yloxy)propoxy]ethoxy]ethyl methanesulfonate [1.4 g (2.4 millimoles)] obtained in Reference Example 7 was subjected to the same reaction as that of Example 5, to give the above-identified compound [560 mg (36%)].

IR (Nujol) cm$^{-1}$: 3270, 3120, 1695, 1585, 1395, 1300, 1115.

NMR (90 MHz, CDCl$_3$) δ: 0.87 (3H), 1.27 (32H), 3.43 (2H), 3.53–3.77 (8H), 4.00 (2H), 4.97 (2H), 5.53 (1H), 6.80 (1H), 8.07 (1H), 8.43 (1H), 8.73 (1H), 9.00 (2H), 10.07 (1H).

EXAMPLE 13

1-Hexyl-3-[2-[2-[3-octadecyloxy-2-(pyrimidin-4-yloxy)propoxy]ethoxy]ethyl]imidazolium chloride 1-Hexylimidazole [304 mg (2 millimoles)] was dissolved in 2-[2-[3-octadecyloxy-2-(pyrimidin-4-yloxy)propoxy]ethoxy]ethyl methanesulfonate [800 mg (1.36 millimole)], and the mixture was heated at 80° C. for 2.5 hours. The mixture was dissolved in a mixture of dichloromethane and ethanol (95:5; 60 ml) and shaken with 30% saline for separation into layers. The lower layer collected was concentrated and purified by silica gel column chromatography [Merck, Art. 7734, 30 g (eluent: chloroform-methanol=9:1–65:25)] to give the above-identified compound [760 mg (82%)].

IR (Neat) cm$^{-1}$: 3370, 2925, 2855, 1580, 1560, 1465, 1390, 1300, 1165, 1115.

NMR (90 MHz, CDCl$_3$) δ: 0.87 (6H), 1.13–1.67 (38H), 1.73–2.03 (2H), 3.43 (2H), 3.60–3.80 (10H), 4.23 (2H), 4.63 (2H), 5.57 (1H), 6.73 (1H), 7.03 (1H), 7.50 (1H), 8.43 (1H), 8.73 (1H), 10.97(1H).

EXAMPLE 14

N-2-[2-[2-[3-Octadecyloxy-2-(pyrimidin-2-yloxy)propoxy]ethoxy]ethoxy]ethyl-N,N,N-trimethylammonium chloride 2-[2-[2-[3-Octadecyloxy-2-(pyrimidin-2-yloxy)propoxy]ethoxy]ethoxy]ethyl methanesulfonate [800 mg (1.32 millimole)] obtained in Reference Example 10 was subjected to the same reaction as that of Example 11 to give the above-identified compound [585 mg (70%)].

IR (Nujol) cm$^{-1}$: 3400, 1575, 1565, 1425, 1310, 1110.

NMR (90 MHz, CDCl$_3$—CD$_3$OD) δ: 0.87 (3H), 1.27 (32H), 3.30 (9H), 3.37–4.10 (18H), 5.43 (1H), 6.97 (1H), 8.50 (2H).

EXAMPLE 15

1-Hexyl-3-[2-[2-[2-[3-octadecyloxy-2-(pyrimidin-2-yloxy)propoxy]ethoxy]ethoxy]ethyl]imidazolium chloride 2-[2-[2-[3-Octadecyloxy-2-(pyrimidin-2-yloxy)propoxy]ethoxy]ethoxy]ethyl methanesulfonate [605 mg (1 millimole)] obtained in Reference Example 10 was subjected to the same reaction as that of Example 13 to give the above-identified compound [510 mg (70%)].

IR (Neat) cm$^{-1}$: 3400, 2925, 2860, 1575, 1565, 1465, 1425, 1310, 1110.

NMR (90 MHz, CDCl$_3$) δ: 0.87 (6H), 1.13–1.63 (38H), 1.70–2.07 (2H), 3.43 (2H), 3.53–3.90 (14H), 4.23 (2H), 4.67 (2H), 5.43 (1H), 6.93 (1H), 7.30 (1H), 7.77 (1H), 8.47 (2H), 10.70 (1H).

TEST EXAMPLE 1

Proliferation-inhibitory effect (IC$_{50}$) of compounds in Examples against human myelocytic leukemia HL-60 cells HL-60 cells (human leukemia cell line) were suspended in GIT medium (Wako Pure Chemicals) containing a test compound to a concentration of $2 \times 10^5$ cells/ml, and 0.2 ml of the suspension was transferred to each well of a microwell plate having 96 wells. After the cultivation was carried out at 37° C. for 20 hours under 5% CO$_2$, 1 μCi [$^3$H]thymidine (5 Ci/mmol) was added, and then the cultivation was continued for further 4 hours. To determine the amount of thymidine incorporated into the cells, an acid-insoluble fraction was collected by a glass filter, and the radioactivity was measured by a liquid scintillation counter. The concentration of the drug which was required for 50% reduction of incorporated radioactivity from that of the control group without medication was taken as the IC$_{50}$ value of the compound.

The IC$_{50}$ values of the compounds of Examples are shown in Table 1.

TABLE 1

| Example No. | IC$_{50}$ (μg/ml) |
|---|---|
| 1 | 0.63 |
| 2 | 1.25 |
| 3 | 0.32 |
| 4 | 2.5 |
| 5 | 0.63 |
| 8 | 1.25 |
| 10 | 0.63 |
| 11 | 1.25 |
| 12 | 2.5 |
| 14 | 2.5 |

TEST EXAMPLE 2

Antitumor activity of compounds in Examples

ICR mice were intraperitoneally inoculated with $1 \times 10^5$ Sarcoma 180 cells per mouse, and then intraperitoneally given 0.33 mg/mouse of a compound of Examples dissolved in physiological saline, three times in total, i.e. 1 hour, 1 day and 2 days after the inoculation. The life-span prolongation ratio* (T/C %) against the control group without medication and the number of surviving mice on the 60th day are shown in Table 2.

TABLE 2

| Example No. | T/C (%) | No. of survivors/ No. of tested animals |
|---|---|---|
| 1 | 200 | 0/5 |
| 3 | 269 | 0/5 |
| 4 | 244 | 0/4 |

*Calculated only on the survival days of died mice.

TEST EXAMPLE 3

Antitumor activity of compounds in Examples

C$_3$H mice were intraperitoneally inoculated with $1 \times 10^4$ murine breast cancer MM46 cells, and then intraperitoneally given a compound of Examples dissolved in physiological saline once a day for 4 days from the 2nd day after the inoculation. The life-span prolongation ratio* (T/C %) against the control group without medication and the number of surviving mice on the 60th day are shown in Table 3.

TABLE 3

| Example No. | Dose (mg/mouse, per administration) | T/C (%) | No. of survivors/ No. of tested animals |
|---|---|---|---|
| 1 | 0.25 | 160 | 4/5 |
| 2 | 0.25 | 174 | 1/5 |
| 6 | 0.25 | 121 | 4/5 |
| 9 | 0.25 | 132 | 1/3 |

*Calculated only on the survived days of died mice

TEST EXAMPLE 4

Antitumor activity of the compound in Example 2

CDF1 mice (5 heads per group) were intraperitoneally inoculated with $1 \times 10^6$ P388 cells per mouse, and then intraperitoneally given 0.5 mg/mouse of the compound in Example 2 dissolved in physiological saline, twice in total, i.e. 1 hour and 5 days after the inoculation. The life-span prolongation ratio (T/C %) against the control group without medication was 151%.

What is claimed is:

1. A compound having the formula:

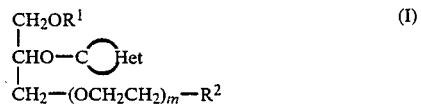

wherein

represents pyrimidinyl, which is unsubstituted or substituted by halogen, C$_{1-6}$ alkyl, C$_{1-6}$ alkylthio, N-C$_{1-6}$ alkylamino, N,N-di-C$_{1-6}$ alkylamino, C$_{1-6}$ alkoxy, hydroxy, hydroxy-C$_{1-6}$ alkyl, amino-C$_{1-6}$ alkyl, carbamoyl or ureido;

R$^1$ represents C$_{10-20}$ alkyl which is unsubstituted or substituted by C$_{3-8}$ cycloalkyl or up to 7 halogen atoms;

R$^2$ represents (i) a tertiary amino group of the formula:

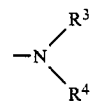

wherein R$^3$ and R$^4$ independently represent C$_{1-6}$ alkyl, or both, taken together with the adjacent nitrogen atom, form 1-pyrrolidinyl, piperidino, morpholino or 1-piperazinyl, each of said groups being unsubstituted or substituted by C$_{1-6}$ alkyl, carboxy, C$_{1-6}$ alkoxycarbonyl, mercapto, hydroxy, hydroxy-C$_{1-6}$ alkyl, amino-C$_{1-6}$ alkyl, carbamoyl or ureido, (ii) a quaternary ammonium group of the formula:

wherein $R^3$, $R^4$ and $R^5$ independently represent $C_{1-6}$ alkyl, or $R^3$, $R^4$ and $R^5$, taken together with the adjacent nitrogen atom, form 1-pyridino, 3-oxazolio, 3-thiazolio, 1-$C_{1-6}$ alkyl-3-imidazolio, 1-pyrimidinio, 1-pyridazinio, 1-quinolinio, 2-isoquinolinio, 1-$C_{1-6}$alkyl-1-pyrrolidinio, 1-$C_{1-6}$ alkyl-1-piperidinio, 4-$C_{1-6}$ alkyl-4-morpholinio or 1-$C_{1-6}$ alkyl-1-piperazinio, each of said groups being unsubstituted or substituted by $C_{1-6}$ alkyl, carboxy, $C_{1-6}$ alkoxycarbonyl, mercapto, hydroxy, hydroxy-$C_{1-6}$ alkyl, amino-$C_{1-6}$alkyl, carbamoyl or ureido, (iii) a heterocyclic group containing a tertiary nitrogen atom selected from the class consisting of 1-($C_{1-6}$ alkyl)pyrrolidin-2- or 3-yl, 1-($C_{1-6}$ alkyl)piperidin-2-, -3- or -4-yl, 4-($C_{1-6}$alkyl)morpholin-2- or -3-yl and 1-($C_{1-6}$alkyl)piperazin-2- or -3-yl, each of said groups being unsubstituted or substituted by $C_{1-6}$ alkyl, carboxy, $C_{1-6}$ alkoxycarbonyl, mercapto, hydroxy, hydroxy-$C_{1-6}$ alkyl, amino-$C_{1-6}$alkyl, carbamoyl or ureido, or (iv) a heterocyclic group containing a quaternary nitrogen atom selected from the class consisting of 1-($C_{1-6}$ alkyl)-2-, -3- or -4-pyridinio, 3-($C_{1-6}$ alkyl)-2-, -4- or -5-oxazolio, 3-($C_{1-6}$ alkyl)-2-, -4- or -5-thiazolio, 1-($C_{1-6}$ alkyl)-2-, -3-, -4-, -5-, -6-, -7- or -8-quinolinio, 2-($C_{1-6}$ alkyl)-1-, -3-, -4-, -5-, -6-, -7- or -8-isoquinolinio, 1,1-di($C_{1-6}$ alkyl)-2- or -3-pyrrolidinio, 1,1-di($C_{1-6}$ alkyl)-2-, -3- or -4-piperidinio, 4,4-di($C_{1-6}$ alkyl)-2- or -3-morpholinio and 1,1,4-tri($C_{1-6}$ alkyl)-2 or -3-piperazinio, each of said groups being unsubstituted or substituted by $C_{1-6}$ alkyl, carboxy, $C_{1-6}$ alkoxycarbonyl, mercapto, hydroxy, hydroxy-$C_{1-6}$alkyl, amino-$C_{1-6}$alkyl, carbamoyl or ureido; and m represents 2 or 3; or a pharmaceutically acceptable salt thereof, wherein said compound represented by the formula (I) can be in the form of a pharmaceutically acceptable salt with an anion or an intramolecular salt with an anion in the molecule of said compound when $R^2$ represents a quaternary ammonium group or a heterocyclic group containing a quaternary nitrogen atom.

2. A compound according to claim 1, wherein $R^2$ represents a tri-$C_{1-6}$ alkylammonium group, a 1-pyridinio group, a 3-thiazolio group or a 1-($C_{1-6}$ alkyl)-3-imidazolio group, said 1-pyridinio, 3-thiazolio and 1-($C_{1-6}$ alkyl)-3-imidazolio groups being unsubstituted or substituted by $C_{1-6}$ alkyl, carboxy, $C_{1-6}$ alkoxy, carbonyl, mercapto, hydroxy, hydroxy-$C_{1-6}$ alkyl, amino-$C_{1-6}$ alkyl, carbamoyl or ureido.

3. A compound according to claim 1, wherein $R^2$ represents a trimethylammonium group.

4. A compound according to claim 1, wherein $R^1$ represents n-octadecyl.

5. A compound according to claim 1, wherein m represents 2.

6. A compound according to claim 1, wherein

represents pyrimidinyl, which is unsubstituted or substituted by halogen, $C_{1-4}$ alkyl, $C_{1-4}$ alkylthio, N-$C_{1-4}$ alkylamino, N,N-di-$C_{1-4}$ alkylamino, $C_{1-4}$ alkoxy, hydroxy, hydroxy-$C_{1-4}$ alkyl, amino-$C_{1-4}$ alkyl, carbamoyl or ureido; and $R^2$ represents (i) a tertiary amino group of the formula:

wherein $R^3$ and $R^4$ independently represent $C_{1-5}$ alkyl, or both, taken together with the adjacent nitrogen atom, form 1-pyrrolidinyl, piperidino, morpholino or 1-piperazinyl, each of said groups being unsubstituted or substituted by $C_{1-4}$ alkyl, carboxy, mercapto, hydroxy, hydroxy-$C_{1-4}$alkyl, amino-$C_{1-4}$alkyl, carbamoyl or ureido, (ii) a quaternary ammonium group of the formula:

wherein $R^3$, $R^4$ and $R^5$ independently represent $C_{1-5}$ alkyl, or $R^3$, $R^4$ and $R^5$, taken together with the adjacent nitrogen atom, form 1-pyridinio, 3-oxazolio, 3-thiazolio, 1-$C_{1-4}$ alkyl-3-imidazolio, 1-pyrimidinio, 1-pyridazinio, 1-quinolinio, 2-isoquinolinio, 1-$C_{1-4}$alkyl-1-pyrrolidinio, 1-$C_{1-4}$ alkyl-1-piperidinio, 4-$C_{1-4}$ alkyl-4-morpholinio or 1-$C_{1-4}$ alkyl-1-piperazinio, each of said groups being unsubstituted or substituted by $C_{1-4}$alkyl, carboxy, mercapto, hydroxy, hydroxy-$C_{1-4}$ alkyl, amino-$C_{1-4}$ alkyl, carbamoyl or ureido, (iii) a heterocyclic group containing a tertiary nitrogen atom selected from the class consisting of 1-($C_{1-4}$ alkyl)pyrrolidin-2- or -3-yl, 1-($C_{1-4}$ alkyl)piperidin-2-, -3- or -4-yl, 4-($C_{1-4}$ alkyl)morpholin-2- or -3-yl and 1-($C_{1-4}$ alkyl)piperazin-2- or -3-yl, each of said groups being unsubstituted or substituted by $C_{1-4}$ alkyl, carboxy, mercapto, hydroxy, hydroxy-$C_{1-4}$ alkyl, amino-$C_{1-4}$ alkyl, carbamoyl or ureido, or (iv) a heterocyclic group containing a quaternary nitrogen atom selected from the class consisting of 1-($C_{1-4}$alkyl)-2-, -3- or -4-pyridinio, 3-($C_{1-4}$ alkyl)-2-, -4- or -5-oxazolio, 3-($C_{1-4}$ alkyl)-2-, -4- or -5-thiazolio, 1-($C_{1-4}$ alkyl)-2-, -3-, -4-, -5-, -6-, -7- or -8-quinolinio, 2-($C_{1-4}$alkyl)-1-, -3-, -4-, -5-, -6-, -7- or -8-isoquinolinio, 1,1-di($C_{1-4}$ alkyl)-2- or -3-pyrrolidinio, 1,1-di($C_{1-4}$ alkyl)-2-, -3- or -4-piperidinio, 4,4-di($C_{1-4}$ alkyl)-2- or -3-morpholinio and 1,1,4-tri($C_{1-4}$ alkyl) 2- or -3-piperazinio, each of said groups being unsubstituted or substituted by $C_{1-4}$ alkyl, carboxy, mercapto, hydroxy, hydroxy-$C_{1-4}$ alkyl, amino-$C_{1-4}$ alkyl, carbamoyl or ureido.

7. A compound according to claim 2, wherein

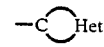

represents pyrimidinyl, which is unsubstituted or substituted by halogen, $C_{1-4}$ alkyl, $C_{1-4}$ alkylthio, hydroxy, hydroxyethyl, aminoethyl, carbamoyl or ureido;

$R^2$ represents (i) a tertiary amino group of the formula:

wherein $R^3$ and $R^4$ independently represent $C_{1-5}$ alkyl, or both, taken together with the adjacent nitrogen atom, form 1-pyrrolidinyl, piperidino, morpholino or 1-piperazinyl, each of said groups being unsubstituted or substituted by $C_{1-4}$ alkyl, hydroxy, hydroxyethyl, aminoethyl, carbamoyl or ureido, or (ii) a quaternary ammonium group of the formula:

wherein $R^3$, $R^4$ and $R^5$ independently represent $C_{1-5}$ alkyl, or $R^3$, $R^4$ and $R^5$, taken together with the adjacent nitrogen atom, form 1-pyridinio, 3-oxazolio, 3-thiazolio, 1-pyridazinio, 1-quinolinio, 2-isoquinolinio, 1-$C_{1-4}$ alkyl-1-pyrrolidinio, 1-$C_{1-4}$ alkyl-1-piperidinio, 4-$C_{1-4}$ alkyl-4-morpholinio or 1-$C_{1-4}$ alkyl-1-piperazinio, each of said group being unsubstituted or substituted by $C_{1-4}$ alkyl, hydroxy, hydroxyethyl, aminoethyl, carbamoyl or ureido.

8. A compound according to claim 1, which is N-2-[2-[3-octadecyloxy-2-(pyrimidin-2-yloxy)propoxy]ethoxy]ethyl-N,N,N-trimethylammonium chloride.

9. A compound according to claim 1, which is 1-[2-[2[-3-octadecyloxy-2-(pyrimidin-2-yloxy)propoxy]ethoxy]ethyl]pyridinio-3-carboxylate.

10. A compound according to claim 1, which is 3-[2-[2-[3-octadecyloxy-2-(pyrimidin-2-yloxy)propoxy]ethoxy]ethyl]thiazolium chloride.

11. A compound according to claim 1, which is N-[2-[2-[3-octadecyloxy-2-(pyrimidin-4-yloxy)propoxy]ethoxy]ethyl-N,N,N-trimethylammonium chloride.

12. A compound according to claim 1, wherein

represents 2-pyrimidinyl.

* * * * *